(12) United States Patent
Lando

(10) Patent No.: US 9,238,134 B2
(45) Date of Patent: *Jan. 19, 2016

(54) ELECTRICAL STIMULATION SYSTEM AND ASSOCIATED APPARATUS FOR SECURING AN ELECTRICAL STIMULATION LEAD IN POSITION IN A PERSON'S BRAIN

(71) Applicant: Advanced Neuromodulation Systems, Inc., Plano, TX (US)

(72) Inventor: Peter R Lando, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 464 days.

This patent is subject to a terminal disclaimer.

(21) Appl. No.: 13/717,268

(22) Filed: Dec. 17, 2012

(65) Prior Publication Data

US 2013/0184793 A1 Jul. 18, 2013

Related U.S. Application Data

(63) Continuation of application No. 13/184,103, filed on Jul. 15, 2011, now Pat. No. 8,337,511, which is a continuation of application No. 11/010,136, filed on Dec. 10, 2004, now Pat. No. 7,981,119.

(60) Provisional application No. 60/528,689, filed on Dec. 11, 2003.

(51) Int. Cl.
*A61B 19/00* (2006.01)
*A61N 1/05* (2006.01)
*A61N 1/36* (2006.01)

(52) U.S. Cl.
CPC ........... *A61N 1/0539* (2013.01); *A61N 1/36017* (2013.01); *A61N 1/36067* (2013.01)

(58) Field of Classification Search
CPC ............ A61N 1/0539; A61N 1/36017; A61N 1/36067
See application file for complete search history.

(56) References Cited

U.S. PATENT DOCUMENTS

| | | | |
|---|---|---|---|
| 5,902,236 A | 5/1999 | Iversen | |
| 5,927,277 A | 7/1999 | Baudino et al. | |
| 6,011,996 A | 1/2000 | Gielen et al. | |
| 6,091,979 A | 7/2000 | Madsen | |
| 6,134,477 A | 10/2000 | Knuteson | |
| 6,210,417 B1 | 4/2001 | Baudino et al. | |
| 6,301,492 B1 | 10/2001 | Zonenshayn | |
| 6,606,521 B2 | 8/2003 | Paspa et al. | |
| 7,204,840 B2 | 4/2007 | Skakoon et al. | |
| 7,450,997 B1 | 11/2008 | Planca et al. | |
| 7,981,119 B2 | 7/2011 | Lando et al. | |
| 8,337,511 B2 | 12/2012 | Lando | |
| 2005/0143799 A1 | 6/2005 | Black et al. | |
| 2005/0246004 A1 | 11/2005 | Cameron et al. | |

*Primary Examiner* — Julian W Woo

(57) ABSTRACT

In one aspect, an apparatus is provided for securing an electrical stimulation lead in position in a person's brain. The apparatus includes a flexible disc comprising a substantially radial slot adapted to secure the lead in position within the brain after implantation. The slot is adapted to elastically expand as the lead is inserted into the slot and is also adapted to elastically contract on the lead to secure the lead in position within the brain after implantation. The apparatus further includes a ring adapted to seat within a burr hole formed in the person's skull. The ring comprises a channel adapted to receive and secure the flexible disc.

18 Claims, 7 Drawing Sheets

ELECTRICAL STIMULATION SYSTEM AND ASSOCIATED APPARATUS FOR SECURING AN ELECTRICAL STIMULATION LEAD IN POSITION IN A PERSON'S BRAIN

CROSS-REFERENCE TO RELATED APPLICATIONS

This application is a continuation of U.S. application Ser. No. 13/184,103, filed Jul. 15, 2011, now U.S. Pat. No. 8,337, 511, which is a continuation of U.S. application Ser. No. 11/010,136, filed Dec. 10, 2004, now U.S. Pat. No. 7,981,119, which claims the benefit of U.S. Provisional Application No. 60/528,689, filed Dec. 11, 2003, which is incorporated herein by reference.

TECHNICAL FIELD OF THE INVENTION

This invention relates generally to electrical stimulation systems designed for implantation into a person's body and more particularly to an electrical stimulation system and associated apparatus for securing an electrical stimulation lead in position in a person's brain.

BACKGROUND

Electrical energy is applied to the brain to treat a variety of clinical conditions such as movement disorders or chronic pain. One method of delivering electrical energy to the brain involves inserting an electrical stimulation lead through a burr hole formed in the skull and then positioning the lead in a precise location adjacent a target area of the brain to be stimulated such that stimulation of the target area causes a desired clinical effect. For example, one desired clinical effect may be cessation of tremor from a movement disorder such as Parkinson's Disease. A variety of other clinical conditions may also be treated with deep brain stimulation, such as essential tremor, tremor from multiple sclerosis or brain injury, or dystonia or other movement disorders. The electrical stimulation lead implanted in the brain is connected to an electrical signal generator implanted at a separate site in the body, such as in the upper chest.

Electrical stimulation leads implanted in the brain require precise placement because of the relatively small size of the target area in the brain and because of the relatively close proximity of other non-targeted anatomic regions in the brain. One method of achieving precise placement is through a stereotactic surgical procedure that uses radiographic or fluoroscopic images of the brain to guide the surgeon to the target area. This may require placement of a three-dimensional frame to the head such that horizontal and vertical coordinates of the target area may be compared to radiographic images and precisely located. Other stereotactic methods may include a frameless procedure. Once the precise location of an electrical stimulation lead in the brain is achieved it is important that the lead remain in its precise position to avoid injury to the brain, reduced effectiveness, or other undesirable effects. An electrical stimulation lead may be particularly prone to being dislodged when a stereotactic frame is disassembled and removed from the head, for example, after insertion of the lead. When the frame is being disassembled and removed from around the insertion site, a doctor, nurse, or other clinician must typically attempt to manually secure the exposed end of the electrical stimulation lead in an attempt to maintain the precise positioning of the lead in the brain. This is difficult, if not impossible, to accomplish in practice.

SUMMARY OF THE INVENTION

In one aspect, an apparatus is provided for securing an electrical stimulation lead in position in a person's brain. The apparatus includes a flexible disc including a substantially radial slot adapted to secure the lead in position within the brain after implantation. The slot is adapted to elastically expand as the lead is inserted into the slot and is also adapted to elastically contract on the lead to secure the lead in position within the brain after implantation. The apparatus further includes a ring adapted to seat within a burr hole formed in the person's skull. The ring includes a channel adapted to receive and secure the flexible disc.

In another aspect, a method is provided for securing an electrical stimulation lead in position in a person's brain. The method includes inserting into a burr hole formed in the person's skull a ring adapted to seat within a burr hole. The ring includes a channel adapted to receive the flexible disc. The slot is adapted to elastically expand as the lead is inserted into the slot and is also adapted to elastically contract on the lead to secure the lead in position within the brain after implantation. The method further includes inserting the lead into a slot of the flexible disc. The slot is adapted to elastically expand as the lead is inserted into the slot and is also adapted to elastically contract on the lead to secure the lead in position within the brain after implantation. The method further includes securing the flexible disc within the channel of the ring to secure the lead in position within the brain after implantation.

In another aspect, an electrical stimulation system is provided for stimulating a person's brain using an electrical stimulation lead implanted in the person's body. The system includes an electrical stimulation lead adapted for implantation in the brain through a burr hole formed in the person's skull, the lead including one or more electrodes operable to stimulate the brain. The system also includes an apparatus for securing the electrical stimulation lead after implantation of the lead in the brain. The apparatus includes a flexible disc including a substantially radial slot adapted to secure the lead in position within the brain after implantation. The slot is adapted to elastically expand as the lead is inserted into the slot and is also adapted to elastically contract on the lead to secure the lead in position within the brain after implantation. The apparatus also includes a ring adapted to seat within a burr hole formed in the person's skull. The ring includes a channel adapted to receive and secure the flexible disc. The system further includes an implantable stimulation source adapted to be coupled to the electrical stimulation lead and to generate electrical signals for transmission to the lead for stimulation of the brain.

In another aspect, a method is provided for implanting an electrical stimulation system into a person's body for stimulating the person's brain using an electrical stimulation lead implanted in the person's brain. The method includes inserting into a burr hole in the person's skull a ring adapted to seat within a burr hole. The ring includes a channel adapted to receive the flexible disc. The slot is adapted to elastically expand as the lead is inserted into the slot and is adapted to elastically contract on the lead to secure the lead in position within the brain after implantation. The method also includes inserting the electrical stimulation lead into a slot of the flexible disc. The slot is adapted to elastically expand as the lead is inserted into the slot and is also adapted to elastically contract on the lead to secure the lead in position within the brain after implantation. The method further includes securing the flexible disc within the channel of the of the ring to secure the lead in position within the brain after implantation.

The method further includes implanting into the human's body a stimulation source adapted to be coupled to the lead and to generate electrical signals for transmission to the lead for stimulation of the brain.

Particular embodiments of the present invention may provide one or more technical advantages. For example, certain embodiments allow the electrical stimulation lead to be securely positioned within the person's brain at any desired angular position within the burr hole. Furthermore, certain embodiments allow the electrical stimulation lead to be securely positioned within the person's brain at any desired position within the burr hole. Certain embodiments substantially prevent movement of the electrical stimulation lead after it has been positioned within the brain, during subsequent removal of any insertion cannula and stereotactic equipment for example. Certain embodiments may provide all, some, or none of these technical advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and advantages thereof, reference is now made to the following description taken in conjunction with the accompanying drawings, in which.

DESCRIPTION OF EXAMPLE EMBODIMENTS

Figure 1A:
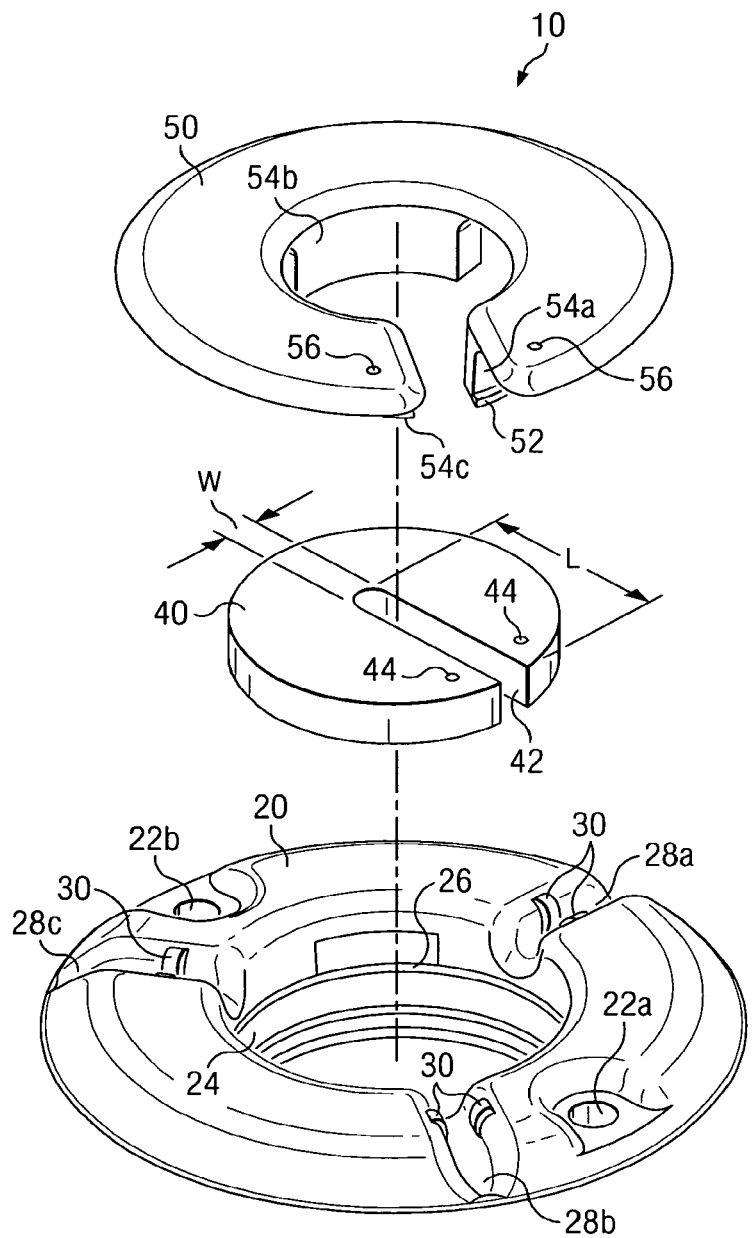
FIG. 1A illustrates an exploded view of an example apparatus for securing an electrical stimulation lead in position in a person's brain.
Figure 1B:
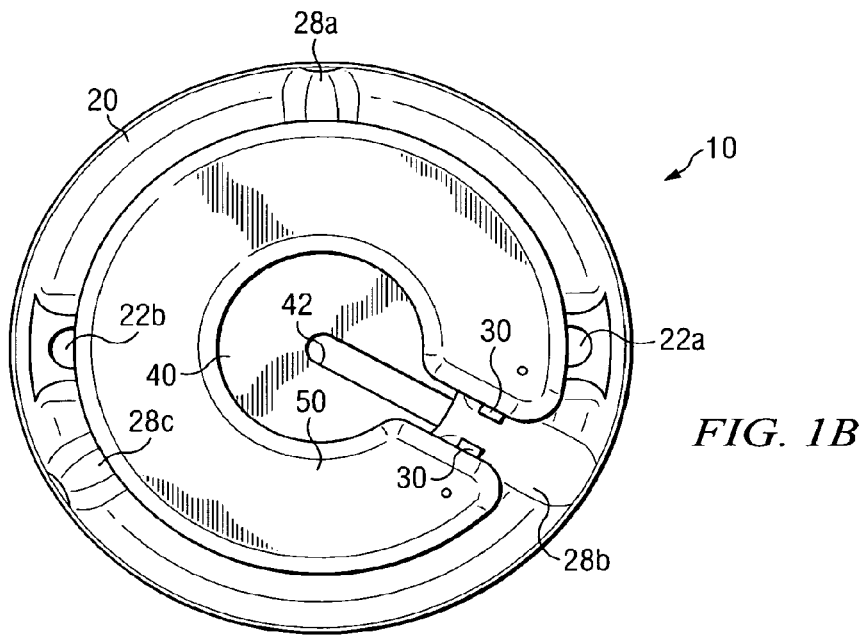
FIG. 1B illustrates a top view of an example apparatus for securing an electrical stimulation lead in position in a person's brain.

FIGS. 1A-1B illustrate an example apparatus 10 for securing an electrical stimulation lead in position in a person's brain, the lead implanted in the person's brain through a burr hole formed in the person's skull. For example, the burr hole may be formed to provide access to the brain for implantation of the electrical stimulation lead for deep brain or other brain stimulation, and apparatus 10 may be used to secure the lead during and after precise positioning of the lead in the brain using a stereotactic or other surgical procedure. The electrical stimulation lead may be a percutaneous lead having one or more circumferential electrodes that emit electrical energy substantially radially in all directions, a laminotomy or "paddle style" lead having one or more directional electrodes that emit electrical energy in a direction substantially perpendicular to a surface of the lead, or any other suitable lead. As described more fully below, the electrodes of the electrical stimulation lead are located at one or more sites along a stimulating portion of the lead having a leading end that enters the skull first and a trailing end that enters the skull thereafter. A connecting portion of the electrical stimulation lead typically couples the stimulating portion of the lead to an appropriate source of electrical stimulation that drives the electrodes of the lead.

In one embodiment, apparatus 10 includes a substantially circular ring 20, a substantially circular flexible disc 40, and a substantially circular cap 50. In other embodiments, ring 20, disc 40, and cap 50 may have other suitable shapes. Ring 20 is configured to seat within the burr hole formed in the skull. Ring 20 may include one or more holes 22 through which sutures, screws, or other suitable fixators may be placed to secure ring 20 to the scalp or skull. In one embodiment, ring 20 includes a channel 24 adapted to receive disc 40 and allow disc 40 to rotate within channel 24. The diameter of channel 24 may be slightly smaller than the diameter of disc 40 such that disc 40 is compressed radially when seated within channel 24. In another embodiment, the diameter of channel 24 may be substantially the same size as the diameter of disc 40 such that disc 40 can rotate within channel 24 with slight resistance. In another embodiment, the diameter of channel 24 may be smaller than the diameter of disc 40 such that disc 40 can rotate within channel 24 with essentially no resistance. Disc 40 may also include one or more holes 44 adapted to receive a tool for removing disc 40 from channel 24 of ring 20. Disc 40 may be formed of any suitable bio-compatible elastomer, polymer, polyurethane, rubber, or other material. In one embodiment, ring 20, disc 40, and cap 50 may be referred to collectively as a "burr hole cover" or a "burr hole cap." In one embodiment, ring 20 may include one or more substantially transverse channels 28 configured to receive the connecting portion of the electrical stimulation lead such that the connecting portion is positioned in a channel 28 to lay substantially flat along the skull. Although three channels 28a, 28b, and 28c are illustrated, any appropriate number of channels 28 may be provided to allow the electrical stimulation lead to be positioned in a selected channel 28 closest to the location of the lead within the burr hole. Each channel 28 may include one or more tabs 30 adapted to grip the connecting portion of the electrical stimulation lead to secure it within channel 28.

Cap 50 is configured to be-removably secured to ring 20 to secure disc 40 in channel 24 and to substantially prevent the upward movement of disc 40 within channel 24. In one embodiment, ring 20 includes a notch 26 adapted receive and engage a tip 52 of one or more tabs 54 of cap 50 to removably secure cap 50 to ring 20. Although three tabs 54a, 54b, and 54c are illustrated, any appropriate number of tabs 54 may be provided. Notch 26 may be a substantially continuous notch around ring 20 or may be a discontinuous notch divided into multiple segments each adapted to receive and engage a corresponding tab 54. Cap 50 may also include one or more holes 56 adapted to receive a tool to aid in coupling cap 50 to and uncoupling cap 50 from ring 20. Ring 20 and cap 50 may be formed of a bio-compatible polymer, plastic, rubber, metal, or any other suitable material. FIG. 1B shows apparatus 10 with cap 50 secured to ring 20.

Disc 40 includes a substantially radial slot 42 adapted to receive and secure the electrical stimulation lead, as described more fully below. In one embodiment, slot 42 extends radially from the center of disc 40 to the perimeter of disc 40, but may be shorter or longer in other embodiments. Width W of slot 42 is smaller than the diameter of the stimulating portion of the electrical stimulation lead and any associated insertion cannula, such as a cannula associated with a needle. In one embodiment, the electrical stimulation lead has a width of approximately $55/1000$ inch, and slot 42 has a natural width of approximately $30/1000$ inch and is adapted to expand to a width of at least approximately $55/1000$ inch to receive and secure the lead, as described more fully below. Slot 42 is adapted to elastically expand as the electrical stimulation lead is inserted into slot 42, and is also adapted to elastically contract on the lead to secure the lead in position in the brain after implantation. Where an insertion cannula is used for insertion of the electrical stimulation lead, this means that slot 42 is: (1) adapted to elastically expand to receive the cannula as the cannula is inserted into slot 42, the lead being inserted into slot 42 via the cannula; and (2) adapted to elastically contract on and continuously grip the cannula until the cannula is removed from the brain after implantation of the lead and, substantially immediately after the cannula is removed, to elastically contract on and continuously grip the lead to secure the lead in position in the brain. For example, a hollow needle may provide such a cannula.

In one embodiment, for any particular distance from the perimeter of disc 40 that is shorter than the length of L of slot 42, disc 40 allows any angular positioning of the electrical stimulation lead within the burr hole because disc 40 can be rotated to receive the lead within slot 42 regardless of the position of the lead. Where slot 42 extends from the perimeter of disc 40 to at least the center of disc 40 as shown, substantially unlimited positioning of the lead within the burr hole is possible (i.e. at any distance from the perimeter of disc 40 and at any angular position).

Figure 2A:
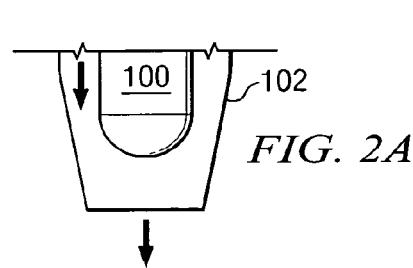
FIGS. 2A-2G illustrate an example of using a slot of a flexible disc of the example apparatus of FIGS. 1A-1B to secure an electrical stimulation lead in position in a person's brain.

FIGS. 2A-2F illustrate an example of using a slot 42 in flexible disc 40 of apparatus 10 to secure an electrical stimulation lead 100 in position in the brain. As shown in FIG. 2A, cannula 102 is inserted into the brain and advanced to the desired depth such that a leading end of cannula 102 is positioned in the brain in appropriate proximity to the target area to be stimulated. Electrical stimulation lead 100 may be inserted along with cannula 102 as shown. Alternatively, electrical stimulation lead 100 may be inserted through cannula 102 after insertion of cannula 102. In either case, the leading end of the stimulating portion of electrical stimulation lead 100 is positioned within the leading end of cannula 102 and the stimulating portion as a whole is positioned adjacent the target area.

Figure 2C:
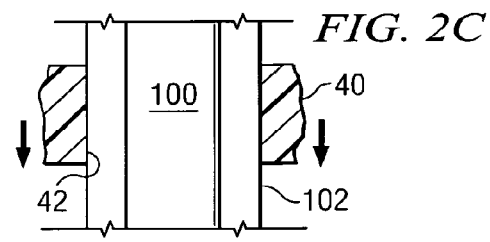
Figure 2B:
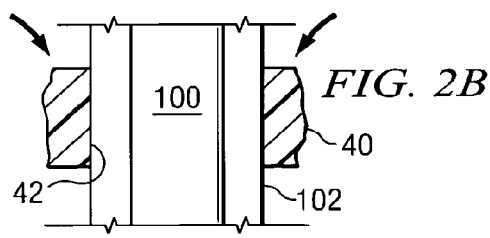
Figure 2D:
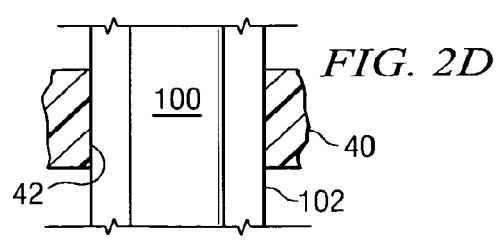

As shown in FIG. 2B, slot 42 of disc 40 is placed about cannula 102 some distance above the burr hole. In one embodiment, disc 40 may be oriented about cannula 102 in any desired manner. As shown in FIG. 2C, disc 40 is moved downward along cannula 102 and snapped or otherwise pressed into and seated within channel 24 of ring 20. Slot 42 elastically contracts on and continuously grips cannula 102 throughout this procedure, such that once electrical stimulation lead 100 has been positioned in the brain and disc 40 has been seated within ring 20 as shown in FIG. 2D, the position of lead 100 may be precisely maintained.

Figure 2E:
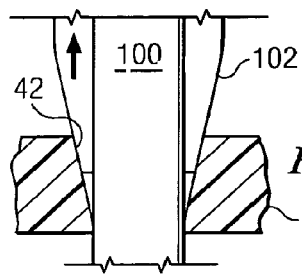
Figure 2F:
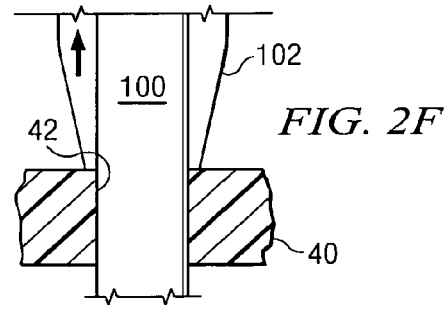
Figure 2G:
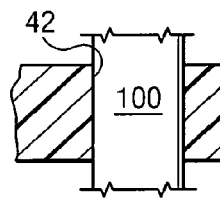

As shown in FIGS. 2E-2G, cannula 102 is removed, leaving electrical stimulation lead 100 in position in the brain. Slot 42 elastically contracts on and continuously grips cannula 102 while cannula 102 is being removed, maintaining the precise positioning of electrical stimulation lead 100 in the brain. Substantially immediately after cannula 102 has been fully removed, slot 42 elastically contracts on and continuously grips the trailing end of the stimulating portion of electrical stimulation lead 100, continuing to maintain the precise positioning of lead 100 in the brain. In one embodiment, disc 40 may be rotated within channel 24 of ring 20 to allow slot 42 to be variably positioned to secure electrical stimulation lead 100 and its associated insertion cannula 102, providing additional flexibility with respect to positioning of lead 100 within the burr hole.

Figure 3A:
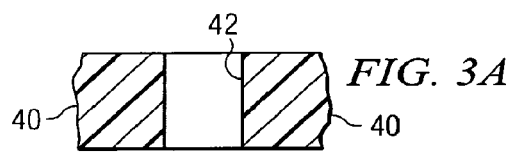
FIGS. 3A-3F illustrate another example of using a slot of a flexible disc of the example apparatus of FIGS. 1A-1B to secure an electrical stimulation lead in position in a person's brain.
Figure 3D:
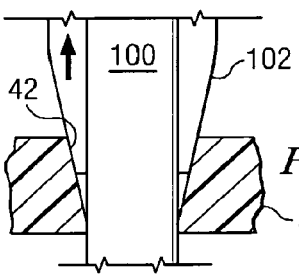
Figure 3B:
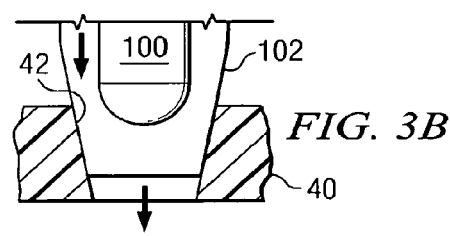
Figure 3E:
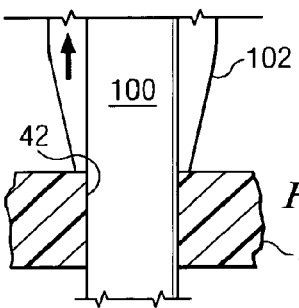
Figure 3C:
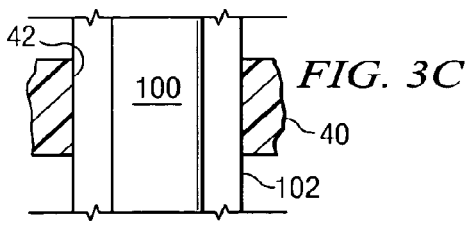

FIGS. 3A-3F illustrate another example of using a slot 42 in flexible disc 40 of apparatus 10 to secure an electrical stimulation lead 100 in position in the brain. Disc 40 is snapped or otherwise pressed into and seated within channel 24 of ring 20. In one embodiment, disc 40 may be rotated within channel 24 of ring 20 to position slot 42 according to the desired position of lead 100 within the burr hole. As shown in FIGS. 3A-3C, cannula 102 is inserted into slot 42 and advanced to the desired depth such that a leading end of cannula 102 is positioned in the brain in appropriate proximity to the target area to be stimulated. Electrical stimulation lead 100 may be inserted along with cannula 102 as shown. Alternatively, electrical stimulation lead 100 may be inserted through cannula 102 after insertion of cannula 102. In either case, the leading end of the stimulating portion of electrical stimulation lead 100 is positioned within the leading end of cannula 102 and the stimulating portion as a whole is positioned adjacent the target area. Slot 42 elastically contracts on and continuously grips cannula 102 throughout this procedure, such that once electrical stimulation lead 100 has been positioned in the brain, that position may be precisely maintained.

Figure 3F:
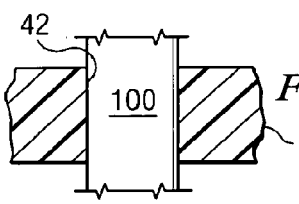

As shown in FIGS. 3D-3F, cannula 102 is removed, leaving electrical stimulation lead 100 in position in the brain. Slot 42 elastically contracts on and continuously grips cannula 102 while cannula 102 is being removed, maintaining the precise positioning of electrical stimulation lead 100 in the brain. Substantially immediately after cannula 102 has been fully removed, slot 42 elastically contracts on and continuously grips the trailing end of the stimulating portion of electrical stimulation lead 100, continuing to maintain the precise positioning of lead 100 in the brain. In one embodiment, disc 40 may be rotated within channel 24 of ring 20 to allow slot 42 to be variably positioned to receive and secure electrical stimulation lead 100 and its associated insertion cannula 102, providing additional flexibility with respect to positioning of lead 100 within the burr hole.

In one embodiment, slot 42 in disc 40 is provided solely for maintaining the precise positioning of electrical stimulation lead 100 in the brain. In this embodiment, slot 42 is not provided to help prevent potential leakage of cerebral-spinal fluid or other substances out of the brain through slot 42 and slot 42 is not intentionally sized to help prevent such leakage. However, in other embodiments, slot 42 may be sized both to help maintain the precise positioning of electrical stimulation lead 100 in the brain and to help prevent leakage of cerebral-spinal fluid or other substances out of the brain.

Figure 4A:
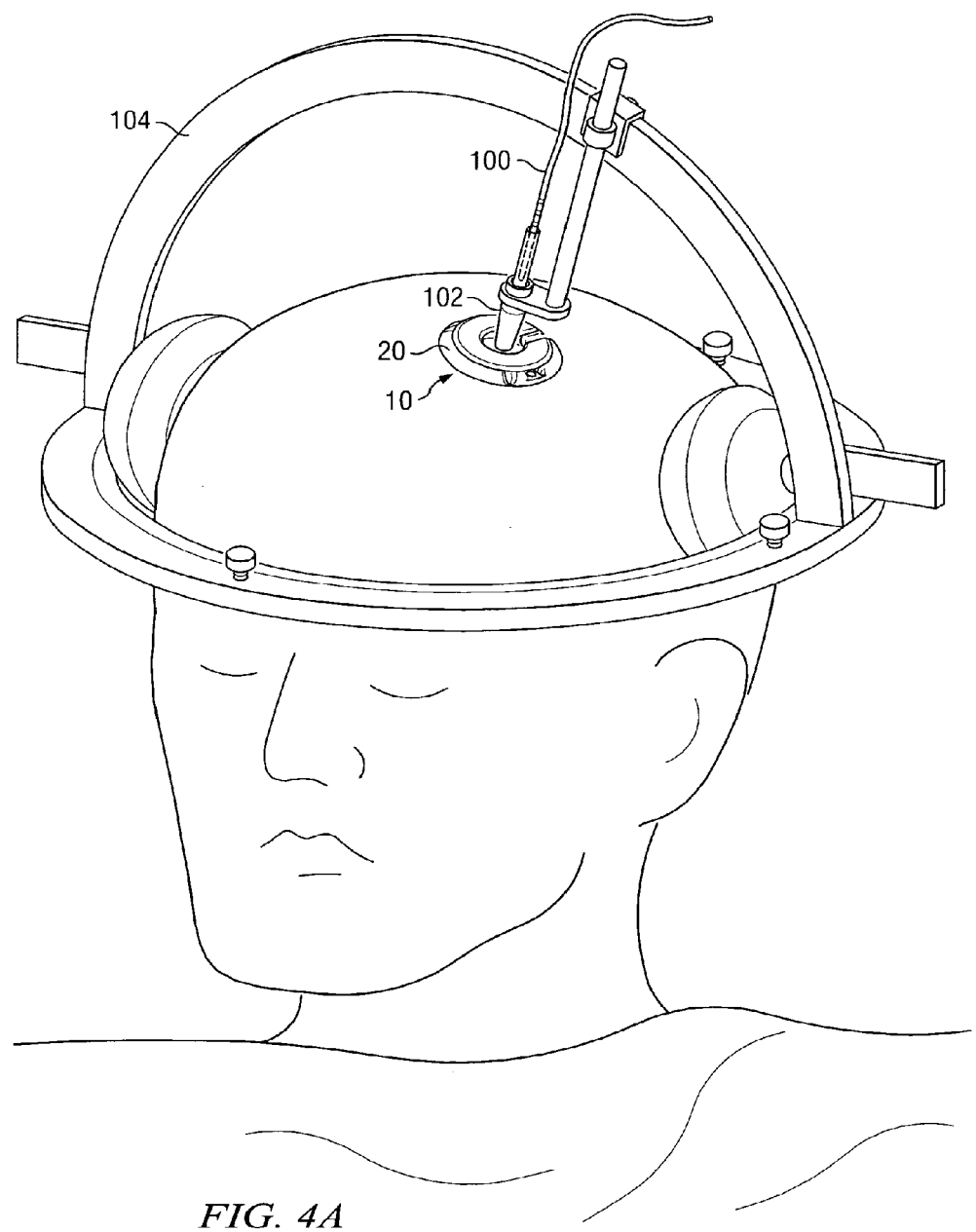
FIGS. 4A-4B illustrate an example of a person undergoing placement of an electrical stimulation lead using the apparatus of FIGS. 1A-1B.
Figure 4B:
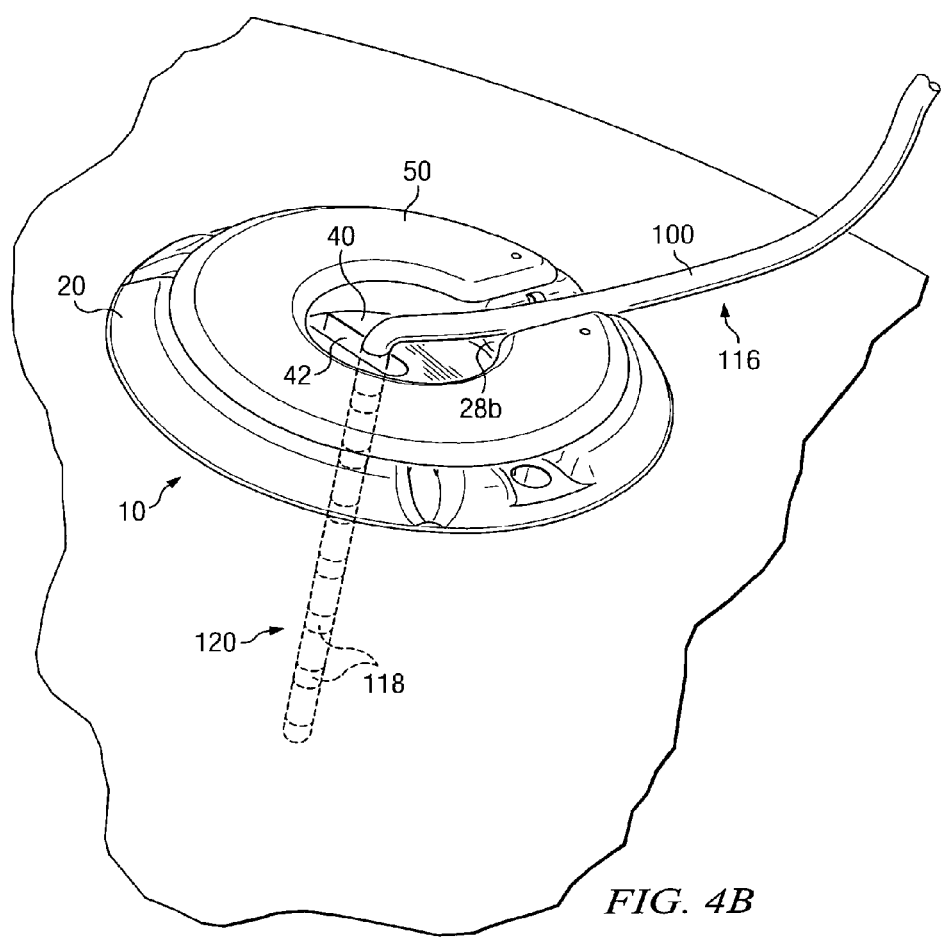

FIGS. 4A-4B illustrate an example of a person undergoing placement of an electrical stimulation lead 100 for brain stimulation using stereotactic equipment 104 to guide lead placement and apparatus 10 to secure lead 100 in position in the person's brain. As can be appreciated from FIG. 4A, electrical stimulation lead 100 is typically coupled to stereotactic equipment 104 during lead placement for increased stability and housed within an insertion cannula 102 for insertion into the brain. Using prior techniques, the precise positioning of electrical stimulation lead 100 in the person's brain may be easily disturbed when lead 100 is uncoupled from stereotactic equipment 104 to allow cannula 102 to be removed from the brain. In contrast, according to the present invention, slot 42 in disc 40 of ring 20 helps to secure electrical stimulation lead 100 in its precise position in the brain despite the uncoupling of lead 100 from stereotactic equipment 104 and removal of cannula 102 from the brain. (Cap 40 is not shown in FIG. 4A for clarity). FIG. 4B shows a close-up view of stimulating portion 112 of electrical stimulation lead 100, with electrodes 114, after insertion through slot 42 in disc 40 via cannula 102 and subsequent removal of cannula 102. The connecting portion 116 of electrical stimulation lead 100 is positioned in a transverse channel 28, such as channel 28b, of ring 20 to lay substantially flat on the skull. Removable cap 50 is coupled to ring 20 to secure disc 40 in channel 24 and to substantially prevent the upward movement of disc 40 within channel 24 when the cannula 102 is removed from slot 42 and to additionally help to prevent both leakage from the burr hole and entry of contaminants into the burr hole where appropriate.

Figure 5A:
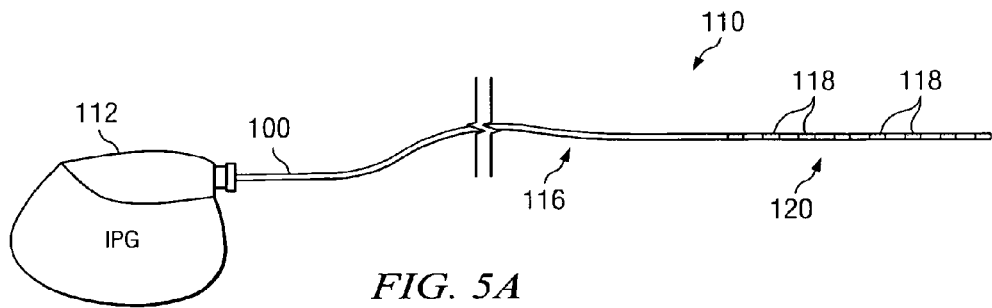
FIG. 5A illustrates an example electrical stimulation system including an implantable pulse generator.
Figure 5B:
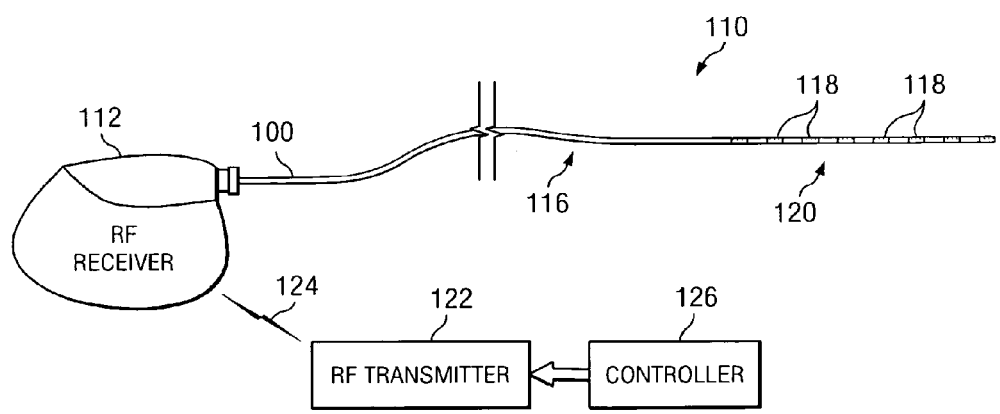
FIG. 5B illustrates an example electrical stimulation system including a wireless receiver.

FIGS. 5A-5B illustrate example electrical stimulation systems 110 for use with apparatus 10. Stimulation system 110 generates and applies a stimulus to a target area of a person's brain. In general terms, stimulation system 110 includes an implantable electrical stimulation source 112 and an implantable electrical stimulation lead 100 for applying the stimulation signal to the target brain tissue. In operation, both of these primary components are implanted in the person's body. Stimulation source 112 is coupled to a connecting portion 116 of electrical stimulation lead 100. Stimulation source 112 controls the electrical signals transmitted to electrodes 118 located on a stimulating portion 120 of electrical stimulation lead 100, located adjacent the target brain tissue, according to suitable signal parameters (e.g., duration, intensity, frequency, etc.). A doctor, the patient, or another user of stimulation source 112 may directly or indirectly input signal parameters for controlling the nature of the electrical stimulation provided.

In one embodiment, as shown in FIG. 5A, stimulation source 112 includes an implantable pulse generator (IPG). An example IPG may be one manufactured by Advanced Neuromodulation Systems, Inc., such as the Genesis® System, part numbers 3604, 3608, 3609, and 3644. In another embodiment, as shown in FIG. 5B, stimulation source 112 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 122 located external to the person's body. The wireless signals are represented in FIG. 5B by wireless link symbol 124. A doctor, the patient, or another user of stimulation source 112 may use a controller 126 located external to the person's body to provide control signals for operation of stimulation source 112. Controller 126 provides the control signals to wireless transmitter 122, wireless transmitter 122 transmits the control signals and power to the wireless receiver of stimulation source 112, and stimulation source 112 uses the control signals to vary the signal parameters of the electrical signals transmitted through electrical stimulation lead 100 to the stimulation site. An example wireless transmitter 122 may be one manufactured by Advanced Neuromodulation Systems, Inc., such as the Renew® System, part numbers 3508 and 3516.

Figure 6:
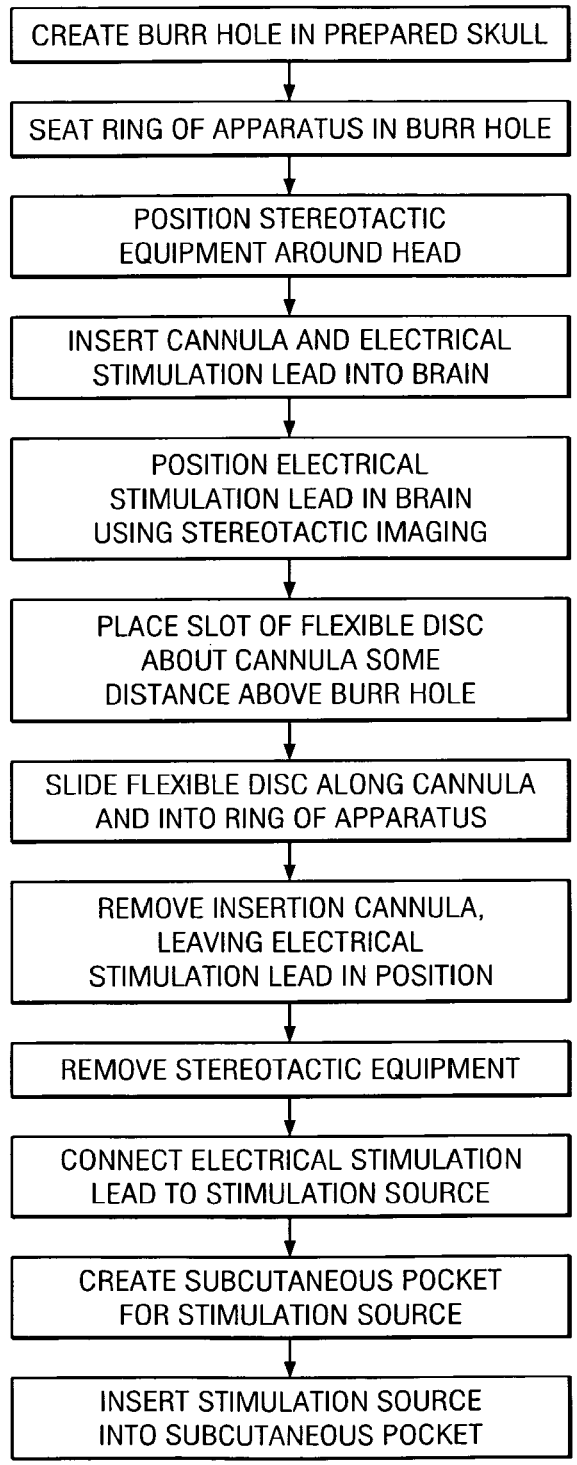
FIG. 6 illustrates example steps for implanting an electrical stimulation system into a person for electrical stimulation of the person's brain.

FIG. 6 illustrates example steps that may be used to implant an example stimulation system 110 into a person for electrical stimulation of the person's brain. The skull is first prepared by exposing the skull and creating a burr hole in the skull. Ring 20 may, but not need, be rotated within the burr hole so that a transverse channel 28 of ring 20 may be properly aligned with connecting portion 116 of electrical stimulation lead 100 when connecting portion 116 is subsequently laid substantially flat along the skull. Ring 20 is then fixed to the scalp or skull using sutures, screws, or other suitable fixators placed through holes 22 of ring 20. Stereotactic equipment 104 suitable to aid in placement of electrical stimulation lead 100 in the brain may be positioned around the head. Insertion cannula 102 for electrical stimulation lead 100 is inserted into the brain. For example, a hollow needle may provide cannula 102. Cannula 102 and electrical stimulation lead 100 may be inserted together or lead 100 may be inserted through cannula 102 after cannula 102 has been inserted. Using stereotactic imaging guidance or otherwise, electrical stimulation lead 100 is then precisely positioned within the brain.

Slot 42 of disc 40 is placed about cannula 102 some distance above the burr hole. In one embodiment, disc 40 may be oriented about cannula 102 in any desired manner. Disc 40 is moved downward along cannula 102 and snapped or otherwise pressed into and seated within channel 24 of ring 20. Once electrical stimulation lead 100 has been positioned in the brain and disc 40 has been seated within ring 20 to secure lead 100, lead 100 is uncoupled from any stereotactic equipment 104, and cannula 102 and any stereotactic equipment 104 are removed. Where stereotactic equipment 104 is used, cannula 102 may be removed before, during, or after removal of stereotactic equipment 104.

Cap 50 of apparatus 10 is removably secured to ring 20 to secure disc 40 in channel 24 of ring 20 and to substantially prevent upward movement of disc 40 as cannula 102 is being removed. As cannula 102 is withdrawn, slot 42 of disc 40 contracts on and continuously grips cannula 102 to help maintain the precise positioning of electrical stimulation lead 100 in the brain. Substantially immediately after cannula 102 has been fully removed, slot 42 contracts on and continuously grips electrical stimulation lead 100 to continue to help maintain the precise positioning of lead 100 in the brain. Connecting portion 116 of electrical stimulation lead 100 is placed into channel 28 within ring 20 of apparatus 10 and laid substantially flat along the skull.

Once electrical stimulation lead 100 has been inserted and secured, lead 100 extends from the lead insertion site to the implant site at which stimulation source 112 is implanted. The implant site is typically a subcutaneous pocket formed to receive and house stimulation source 112. The implant site is usually positioned a distance away from the insertion site, such as near the buttocks or another place in the torso area. Once all appropriate components of stimulation system 110 are implanted, these components may be subject to mechanical forces and movement in response to movement of the person's body. A doctor, the patient, or another user of stimulation source 112 may directly or indirectly input signal parameters for controlling the nature of the electrical stimulation provided.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 110 into a person for electrical stimulation of the person's brain.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method for implanting an electrical stimulation lead in position to stimulate tissue in a person's brain, comprising:
   inserting, into a burr hole formed in the person's skull, a burr hole ring system adapted to seat within the burr hole, wherein (i) the burr hole ring system comprises a lead securing member comprising respective opposing surfaces, and (ii) the lead securing member is adapted to contract to secure the electrical stimulation lead between the respective opposing surfaces;
   inserting a cannula through the lead securing member;
   engaging the cannula by the lead securing member to secure the cannula between the respective opposing surfaces;
   positioning the electrical stimulation lead through the cannula such that electrodes of the lead are disposed relative to a selected area of the person's brain to apply stimulation pulses to the selected area; and
   withdrawing the cannula while retaining the electrical stimulation lead in place, wherein the lead securing member automatically contracts about the stimulation lead as the cannula is withdrawn to hold the stimulation lead in place to stimulate the selected area of the person's brain.

2. The method of claim 1 wherein the burr hole ring system comprises a burr hole ring that is adapted to be secured to the patient's skull and the lead securing member is adapted to be placed within the burr hole ring.

3. The method of claim 2 further comprising:
   securing the burr hole ring with surgical screws to the patient's skull; and
   placing the lead securing member within the burr hole ring after securing the burr hole ring to the patient's skull.

4. The method of claim 2 wherein the lead securing member is adapted to permit positioning of the respective opposing surfaces at any desired angular orientation relative to the burr hole ring.

5. The method of claim 2 wherein the burr hole ring is adapted to apply a circumferential compression to the lead securing member when the lead securing member is placed within the burr hole ring.

6. The method of claim 1 wherein the respective opposing surfaces extend from a perimeter position on the lead securing member to an interior portion of the lead securing member.

7. A method for implanting an electrical stimulation lead in position to stimulate tissue in a person's brain, comprising:
   inserting, into a burr hole formed in the person's skull, a burr hole ring system adapted to seat within the burr hole, wherein (i) the burr hole ring system comprises a lead securing member comprising respective opposing surfaces, and (ii) the lead securing member is adapted to contract to secure the electrical stimulation lead between the respective opposing surfaces;
   inserting an implant tool through the lead securing member;
   engaging the implant tool by the lead securing member to secure the implant tool between the respective opposing surfaces;
   positioning the electrical stimulation lead through the implant tool such that electrodes of the lead are disposed relative to a selected area of the person's brain to apply stimulation pulses to the selected area; and
   withdrawing the implant tool while retaining the electrical stimulation lead in place, wherein the lead securing member automatically contracts about the stimulation lead as the implant tool is withdrawn to hold the stimulation lead in place to stimulate the selected area of the person's brain.

8. The method of claim 7 wherein the burr hole ring system comprises a burr hole ring that is adapted to be secured to the patient's skull and the lead securing member is adapted to be placed within the burr hole ring.

9. The method of claim 8 further comprising:
   securing the burr hole ring with surgical screws to the patient's skull; and
   placing the lead securing member within the burr hole ring after securing the burr hole ring to the patient's skull.

10. The method of claim 8 wherein the lead securing member is adapted to permit positioning of the respective opposing surfaces at any desired angular orientation relative to the burr hole ring.

11. The method of claim 8 wherein the burr hole ring is adapted to apply a circumferential compression to the lead securing member when the lead securing member is placed within the burr hole ring.

12. The method of claim 7 wherein the respective opposing surfaces extend from a perimeter position on the lead securing member to an interior portion of the lead securing member.

13. A method for implanting an electrical stimulation lead in position to stimulate tissue in a person's brain, comprising:
   inserting, into a burr hole formed in the person's skull, a burr hole ring system adapted to seat within the burr hole, wherein (i) the burr hole ring system comprises a lead securing member comprising respective opposing surfaces, and (ii) the lead securing member is adapted to elastically expand to receive the lead securing member and to elastically contract to secure the electrical stimulation lead between the respective opposing surfaces;
   inserting an implant tool through the lead securing member;
   engaging the implant tool by the lead securing member to secure the implant tool between the respective opposing surfaces;
   positioning the electrical stimulation lead through the implant tool such that electrodes of the lead are disposed relative to a selected area of the person's brain to apply stimulation pulses to the selected area; and
   withdrawing the implant tool while retaining the electrical stimulation lead in place, wherein the lead securing member automatically contracts about the stimulation lead as the implant tool is withdrawn to hold the stimulation lead in place to stimulate the selected area of the person's brain.

14. The method of claim 13 wherein the burr hole ring system comprises a burr hole ring that is adapted to be secured to the patient's skull and the lead securing member is adapted to be placed within the burr hole ring.

15. The method of claim 14 further comprising:
   securing the burr hole ring with surgical screws to the patient's skull; and
   placing the lead securing member within the burr hole ring after securing the burr hole ring to the patient's skull.

16. The method of claim 14 wherein the lead securing member is adapted to permit positioning of the respective opposing surfaces at any desired angular orientation relative to the burr hole ring.

17. The method of claim 14 wherein the burr hole ring is adapted to apply a circumferential compression to the lead securing member when the lead securing member is placed within the burr hole ring.

18. The method of claim 13 wherein the respective opposing surfaces extend from a perimeter position on the lead securing member to an interior portion of the lead securing member.

* * * * *